United States Patent
Babel et al.

(10) Patent No.: US 8,733,148 B2
(45) Date of Patent: May 27, 2014

(54) METHOD FOR CALIBRATING AND/OR ADJUSTING A SENSOR, ESPECIALLY AN ELECTROCHEMICAL, ELECTROPHYSICAL OR OPTICAL SENSOR, AND CORRESPONDING SENSOR

(75) Inventors: Wolfgang Babel, Weil der Stadt (DE); Detlev Wittmer, Maulbronn (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 909 days.

(21) Appl. No.: 12/226,667

(22) PCT Filed: Apr. 3, 2007

(86) PCT No.: PCT/EP2007/002992
§ 371 (c)(1),
(2), (4) Date: Aug. 5, 2009

(87) PCT Pub. No.: WO2007/124834
PCT Pub. Date: Nov. 8, 2007

(65) Prior Publication Data
US 2009/0293580 A1 Dec. 3, 2009

(30) Foreign Application Priority Data
Apr. 28, 2006 (DE) .......... 10 2006 020 480
Jul. 15, 2006 (DE) .......... 10 2006 032 905

(51) Int. Cl.
*G01D 18/00* (2006.01)

(52) U.S. Cl.
USPC .......... 73/1.02

(58) Field of Classification Search
None
See application file for complete search history.

(56) References Cited

U.S. PATENT DOCUMENTS

| | | | |
|---|---|---|---|
| 4,760,250 A | 7/1988 | Loeppert | |
| 4,799,559 A | 1/1989 | Murdter | |
| 5,621,406 A | 4/1997 | Goetzinger | |
| 5,814,280 A * | 9/1998 | Tomita et al. | 422/82.01 |
| 7,062,308 B1 * | 6/2006 | Jackson | 600/361 |
| 7,063,681 B1 * | 6/2006 | Peery | 604/60 |

FOREIGN PATENT DOCUMENTS

| | | |
|---|---|---|
| EP | 0 283 704 A2 | 9/1988 |
| EP | 0 775 913 A1 | 5/1997 |
| WO | 9610297 A1 | 4/1996 |
| WO | WO 2005/061995 A1 | 7/2005 |

OTHER PUBLICATIONS

German Search Report, German PTO, Munich, Mar. 1, 2013.

* cited by examiner

Primary Examiner — Robert R Raevis
(74) Attorney, Agent, or Firm — Bacon & Thomas, PLLC

(57) ABSTRACT

A method for calibrating and/or adjusting a sensor, especially an electrochemical, electrophysical or optical sensor, wherein the sensor has an evaluating electronics, which is embodied in such a manner, that a signal produced by the sensor is essentially non-changeable by a subsequent transmission. The sensor is calibrated and/or adjusted at a site other than a later measuring location or a later measuring environment or the like.

16 Claims, 4 Drawing Sheets

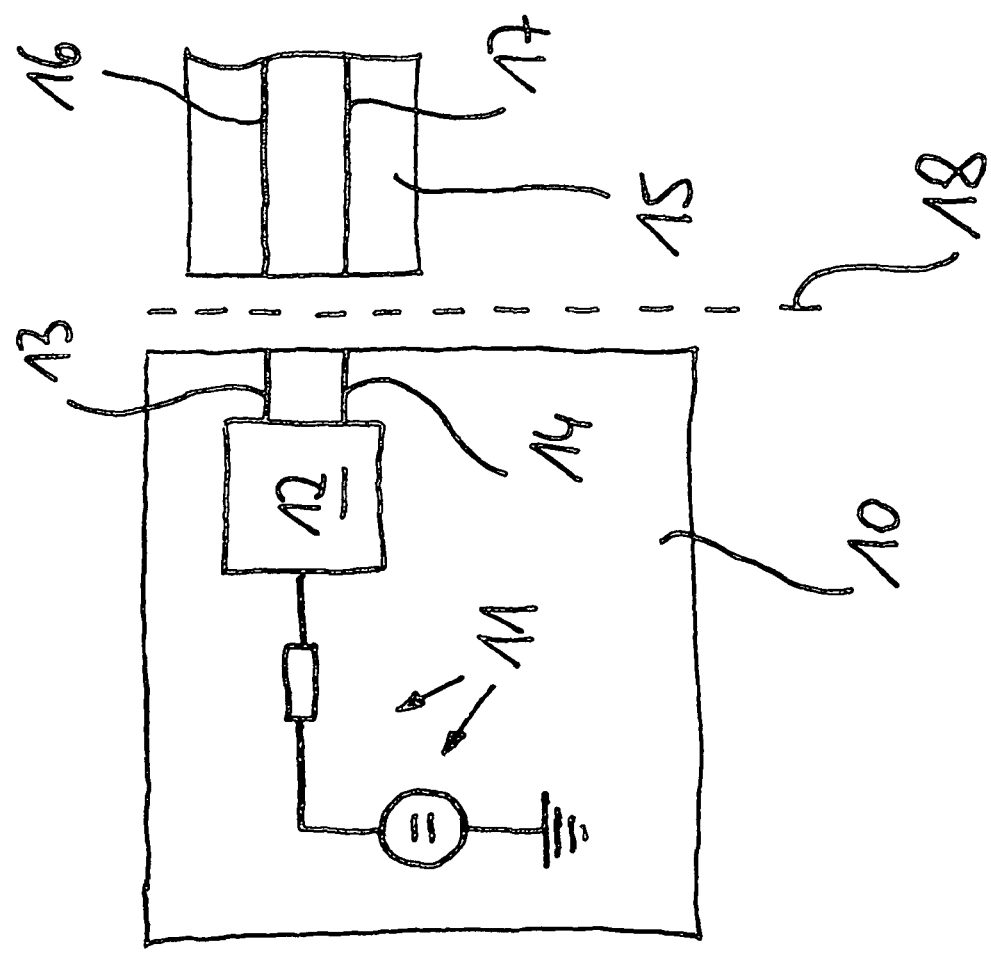

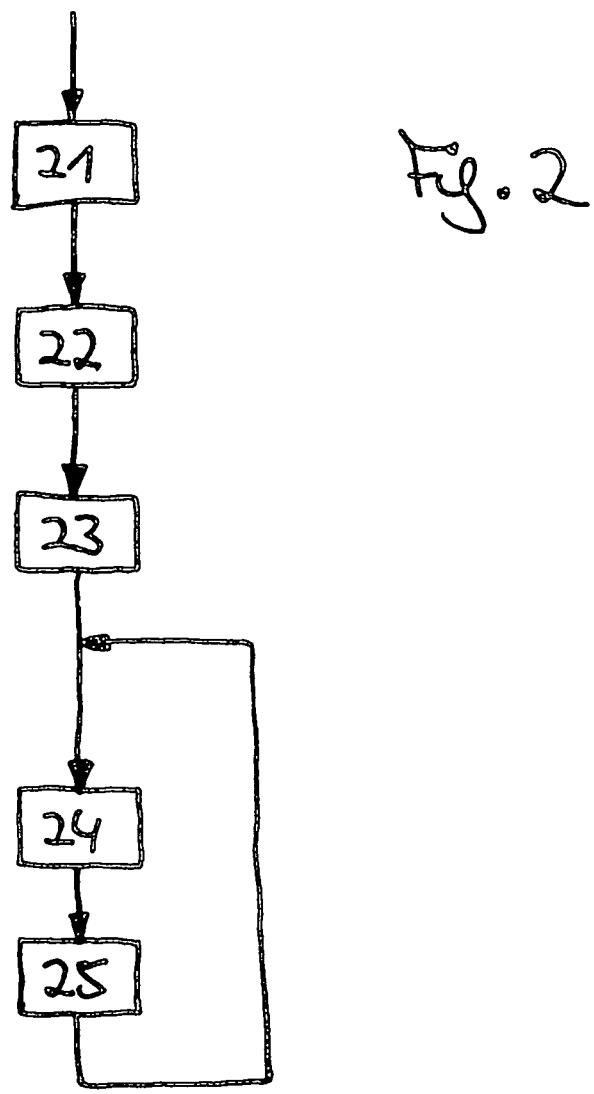

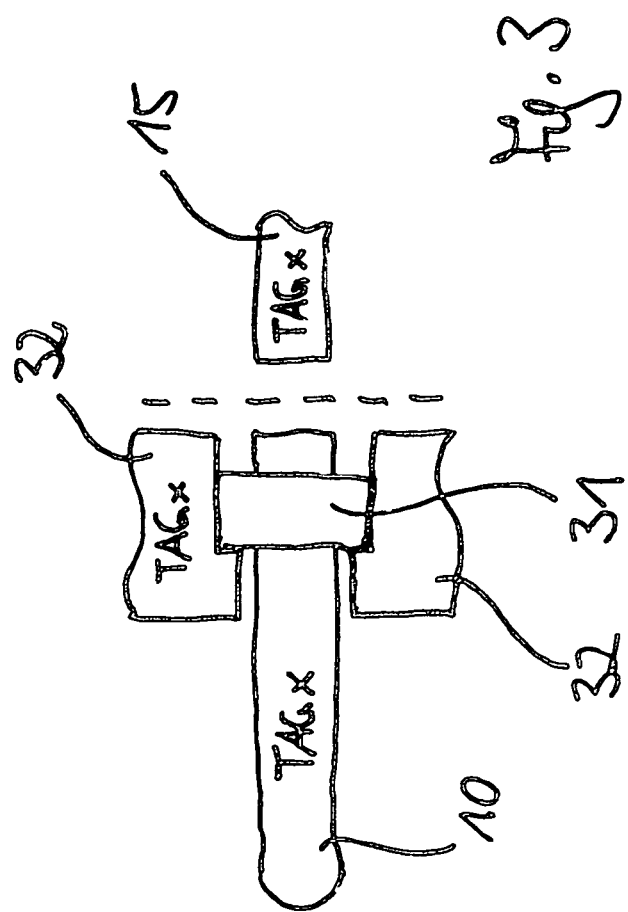

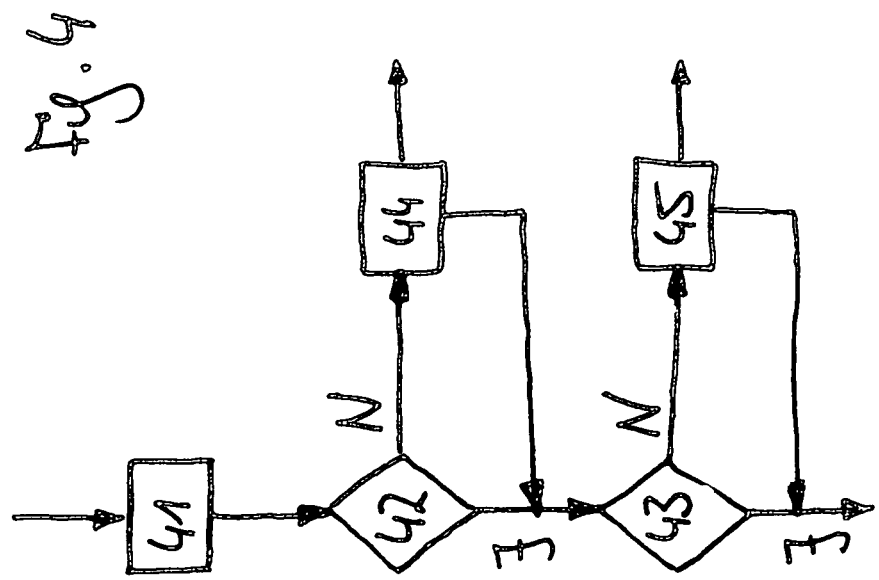

METHOD FOR CALIBRATING AND/OR ADJUSTING A SENSOR, ESPECIALLY AN ELECTROCHEMICAL, ELECTROPHYSICAL OR OPTICAL SENSOR, AND CORRESPONDING SENSOR

TECHNICAL FIELD

The invention relates to method for calibrating and/or adjusting a sensor, especially an electrochemical, electrophysical or optical sensor, wherein the sensor includes an evaluating electronics, which is embodied in such a manner, that the signal produced by the sensor is essentially non-changeable by a subsequent transmission. Furthermore, the invention relates to corresponding sensors.

BACKGROUND DISCUSSION

Electrochemical sensors are known, which are applied, for example, for monitoring the production of sulfuric acid. In order that such a sensor can deliver correct measured values, it must be calibrated and/or adjusted. "Calibrating" refers, in such case, usually, to the determining of a deviation of the measured value measured by the sensor from the correct, measured value, while "adjusting" refers, usually, to the correcting of the measured value measured by the sensor to the correct, measured value. This calibrating and/or adjusting is, in the case of known sensors, put into practice by first installing the sensors at their measuring locations, so that they can then be calibrated and/or adjusted there. Clearly, such on-site calibrating and/or adjusting are/is connected with considerable effort.

Furthermore, most often, a plurality of sensors are in use in such a production plant, wherein, in the case of a defect in one of the sensors, frequently, an immediate replacement of the defective sensor is required. For this purpose, most often, a plurality of new and/or used sensors are stored, in order to assure a fast replacement. This large number of sensors, as well as the different types of the sensors, introduces the risk, that, especially in the case of an immediately required replacement, a sensor is installed, which is not the correct replacement-sensor, but, instead, for example, an incorrect sensor type.

SUMMARY OF THE INVENTION

An object of the invention is to provide methods and sensors overcoming the above disadvantages and problems.

This object is achieved by a method which produces a signal which is essentially non-changeable by a subsequent transmission, and calibrating and/or adjusting the sensor at a site other than a later measuring location or a later measuring environment or the like. The sensor is assigned a tag-number, which designates a later measuring location or a later measurement environment or the like.

Advantageous further developments of the invention are set forth in the

BRIEF DESCRIPTION OF THE DRAWINGS

Other features, opportunities for application and advantages of the invention will become evident from the following description of examples of embodiments of the invention, as illustrated in the figures of the drawing. In such case, all described or shown features form, alone or in any combination, the subject matter of the invention, independently of their summary in the patent claims or their dependencies therein, as well as independently of their formulation or depiction, respectively, in the description or in the drawing.

FIG. 1 shows a schematic drawing of an example of an embodiment of a sensor of the invention;

FIG. 2 shows a schematic block diagram of an example of an embodiment of a method for using the sensor of FIG. 1;

FIG. 3 shows a schematic drawing of the sensor of FIG. 1 in an associated holding apparatus; and FIG. 4 shows a schematic block diagram of an example of an embodiment of a method for operating the sensor of FIG. 1.

DETAILED DISCUSSION

FIG. 1 shows a sensor 10, which can be, especially, an electrochemical sensor, for example, a pH-value sensor. The sensor 10 includes a measuring unit 11, which can be, for example, a pH-measuring, glass-electrode. Measuring unit 11 is connected with an evaluating electronics 12, which can include, for example, a microprocessor.

The evaluating electronics 12 is provided for conditioning, and converting into a digital signal, the electrical signal provided by the measuring unit 11. Conditioning of the analog signal can include, among other things, amplification of the signal. Furthermore, the evaluating electronics 12 can intermediately store the obtained, digital signal.

It is to be noted, that the mentioned conversion into a digital signal is not absolutely necessary. Essential is that, contained in the evaluating electronics 12, are all those functions and all those electronic components having an essential influence on the calibrating and/or adjusting of the sensor 10. This will be explained below in greater detail.

The evaluating electronics 12 is connected with at least two lines 13, 14. Via the first line 13, the evaluating electronics 12 and, if conditions require, also the measuring unit 11, are supplied with electrical energy. Via the second line 14, digital signals are transmitted in the two directions, to and from the evaluating electronics 12.

Sensor 10 can be connected via a coupling (not shown) with a cable 15. Contained in the cable 15 are two lines 16, 17, which are assigned to the lines 13, 14 of the sensor 10. The electrical connection of the two lines 16, 17 of the cable 15 with the two lines 13, 14 of the sensor 10 can be accomplished inductively, for example. Via the cable 15, the sensor 10 can, for example, be connected with a display device and/or with a more extensive, measured-value processing system. E.g., cable 15 can be connected via a so-called common data interface (CDI) to a USB-port of a personal computer.

Present between sensor 10 and cable 15 is an interface 18. There, on the one hand, a certain electrical voltage can be fixedly predetermined, with which the sensor 10 is supplied with electrical energy. On the other hand, the kind and manner of the digital signals exchanged between the sensor 10 and the cable 15 can, there, be fixedly predetermined.

Sensor 10 is produced by a manufacturer and delivered to a customer. The customer can use the sensor 10 in a plant, for example, in a plant for production of sulfuric acid. There, sensor 10 is connected with the cable 15, so that the measured values measured by the sensor 10 can, via the cable 15, for example, be displayed or, in other manner, be further processed e.g. by a personal computer.

FIG. 2 illustrates a method for applying or employing the sensor 10 at the customer's plant. It is assumed in the subsequent description of FIG. 2, that this is a case, in which the sensor 10 is a newly manufactured sensor 10, which was supplied by the manufacturer to the customer. It is, however, to be noted, that the method of FIG. 2 is applicable, in corresponding manner, also to a sensor, which is not new, but, instead, had been used at least once before.

In a first step 21, the serial number of the sensor 10, as well as, if the situation requires, further data of the sensor 10 on the side of the customer, is/are stored in a database. The serial number provides, in such case, a unique identification of the sensor 10 currently of interest. This first step 21 can be performed at any location, and, therefore, independently of the measuring location of the sensor 10.

Thereafter, in a step 22, a tag-number is assigned to the sensor 10. This tag-number is likewise stored in the database, and, indeed, associated to such sensor 10. Also this second step 22 can be performed at any location and, therefore, independently of the measuring location of the sensor 10.

The tag-number can, in such case, be a designation of a measuring location, at which the sensor 10 is permitted to be used. Alternatively, the tag-number can be a designation of a measuring environment, in which the sensor 10 is permitted to be used. Alternatively, the tag-number can also be a designation of a type of measurement, for which the sensor 10 is permitted to be used. As an example, the tag-number can be a designation that the sensor 10 is permitted to be used only in the context of sulfuric acid production.

Furthermore, the tag-number can represent a kind of pooling function, which brings together a number of the above options in any manner.

In a subsequent step 23, the sensor 10 of interest is subjected to a calibrating and/or adjusting. This calibrating and/or adjusting are/is accomplished, in such case, not at the intended measuring location within the plant of the customer. The calibrating and/or adjusting are/is accomplished, thus, in the already mentioned example, not within the plant for production of sulfuric acid. Instead, the calibrating and/or adjusting can be done at any other site—thus, someplace completely independent of the later, measuring location. Especially, the calibrating and/or adjusting of the sensor 10 can be performed in a laboratory.

This ability to perform the calibrating and/or adjusting of the sensor 10 "anywhere" is made possible by the embodying of the sensor 10 according to FIG. 1. Especially, by the embodying of the evaluating electronics 12 in such a way, that, as much as possible, all influences affecting the calibrating and/or adjusting are taken into consideration within the evaluating electronics 12 and, thus, within the sensor 10, in order to achieve, that the signal produced by the sensor 10, can, in subsequent transmission, essentially, no longer be corrupted. This embodying of the sensor 10 represents, lastly, a placing of the measurement section, such that it lies entirely within the sensor 10.

Sensor 10 issues, thus, to the interface 18 a signal, which, essentially, can no longer be disturbed, or altered by subsequent transmission. Thus, the coupling and the subsequent cable 15 have—when at all—only a small influence on the transmitted signals. In every case, this influence is so small, that a corruption of the transmitted signals does not take place.

If the signal produced by the sensor 10 is—such as was explained—a digital signal, then, additionally, algorithms can be applied to the digital signal for error detection and/or correction.

Therewith, it is not necessary to take into consideration, in the calibrating and/or adjusting of the sensor 10, transmission occurring after the sensor 10. Through the accommodating of the entire measurement section within the sensor 10, the sensor 10 can then be calibrated and/or adjusted independently of its later use, especially independently of the later measuring location, the cable 15 used, etc.

The calibrating and/or adjusting of the sensor 10 are/is accomplished, thus, not on-site, but, instead, completely independently of the later location of use of the sensor 10.

The calibrating data produced in the calibrating and/or adjusting of the sensor 10 are stored in the sensor 10 for later use. On occasion, the calibrating data can also be stored in the database of the customer.

It is to be noted, that, also, already at the manufacturer, a calibrating and/or adjusting of the sensor 10 can be performed. In this case, the customer can either—such as above explained—perform its own, additional calibrating and/or adjusting, or it can accept the calibrating and/or adjusting done by the manufacturer. In the second case, this accepting can, in turn, occur "anywhere", thus, especially, completely independently of the later measuring location of the sensor 10.

Thereafter, it is possible, that the sensor 10 will be stored over a longer period of time at the location of customer. It is understood that the steps 21, 22 and 23 can also be ordered differently.

At some time, the sensor 10 will come to be used, in a step 24. The kind and manner of installation of the sensor 10 in the plant of the customer is, in such case, still to be explained on the basis of FIGS. 3 and 4, which will be considered below. In the installed state, the sensor 10 is initialized and synchronized. Thereafter, sensor 10 is able to perform measurements and forward ascertained, measured values via the cable 15. On occasion, measured values of the sensor 10 are also stored. Likewise, an option is that the sensor 10 performs a self-diagnosis or the like.

Following a predetermined period of operation, or in the case of occurrence of an error, or for other reasons, the sensor 10 is removed, in a subsequent step 25, from the plant. Then, a cleaning and/or regeneration of the sensor 10 can be done. Thereafter, the sensor 10 is calibrated and/or adjusted anew. This renewed calibrating and/or adjusting can, in such case, be performed in the same manner as was explained already in connection with step 23. The renewed calibrating and/or adjusting are/is done, again, away from the plant, thus "anywhere", for example, in a laboratory.

Thereafter, use of the sensor 10 is continued with step 24. The sensor 10 is, thus, again installed in the plant of the customer and comes there, again, into use.

The described sequence of the steps 24 and 25 can, in such case, basically, be repeated as often as desired. All produced data, especially calibration data, can, in such case, be stored in the associated database of the customer.

As was explained, the sensor 10 of interest is permitted, for example, to be used only in a certain measuring environment. Thus, it is to be assured, that one and the same sensor 10 is used, for example, always only in the context of sulfuric acid production, and not, in between, for example, in connection with the manufacture of food. As likewise explained, to this end, a certain tag-number is assigned to the sensor 10 of interest.

On the basis of FIG. 3, installation of the sensor 10 of interest in the plant of the customer will now be explained. To this end, sensor 10 and cable 15, as described on the basis of FIG. 1, are illustrated in FIG. 3. Additionally, sensor 10 is provided with a holding part 31, which has, for example, a ring-like form. Associated with this holding part 31 is a holding apparatus 32, which is provided for affixing the sensor 10. The holding apparatus 32, which is frequently also referred to as an armature, which may be a retractable assembly, is, in such case, fitted in such a manner to the holding part 31, that the sensor 10, together with the holding part 31, can be inserted or introduced into the holding apparatus 32, so that, thereafter, the sensor 10 with the holding part 31 is secured fixedly within the holding apparatus 32. Therewith, the sensor 10 can, with the aid of the holding apparatus 32, be securely installed within the plant of the customer.

It is assumed, that the sensor 10 has the tag-number TAGx. This tag-number TAGx is applied, in some way and manner, visibly on or at the sensor 10. For example, the tag-number can be printed or engraved on the sensor 10. Likewise, a component of synthetic material or some other material can provided, on which the tag-number is printed or engraved, and which is, for example, connected clip-like with the sensor 10. Alternatively, the component can also be connected fixedly with the sensor 10, so that it cannot be lost. Furthermore, an option is to provide the sensor 10 with an RFID-chip, in which the tag-number is stored (RFID=radio frequency identification). In this case, the tag-number can be made visible with the help of a suitable read-out device. Furthermore, an option is, with the help of short-range data-radio, to read-out the tag-number electrically stored in the sensor 10, for example, with the aid of Bluetooth- or WLAN-technology (WLAN=wireless local area network). Of course, also, still other options are thinkable for associating the tag-number visibly with the sensor 10.

In corresponding manner, the tag-number TAGx is also visibly placed on that holding apparatus 32, in which the sensor 10 of interest is to be later installed. Since the tag-number—as was explained—designates the measuring location or the measuring environment, in which a certain sensor is permitted to be used, the holding apparatus 32 can be provided earlier with the assigned tag-number. In the explained example, the holding apparatus 32 can have that tag-number, which designates a measuring location or a measuring environment in the case of sulfuric acid production.

Correspondingly, also cable 15 is provided with the tag-number TAGx. Also this tag-number can be applied visibly earlier on the cable 15, such as this has been explained in the connection with the sensor 10.

For the installation of the sensor 10, it is then only necessary, that a service person look for that holding apparatus 32 of a plurality of holding apparatuses, which bears the same tag-number as the sensor 10 of interest. There, the service person can install the sensor 10. The same is true for the cable 15. Also, as a result, it is only necessary, that the service person connect the cable 15 with the same tag-number to the sensor 10.

Conversely, an option, in equal manner, is that the service person retrieves from a plurality of sensors, that sensor 10, which bears the same tag-number as a certain holding apparatus 32. Into this holding apparatus 32, the service person can then install the assigned sensor 10. As regards the cable 15, it is, also in this case, only necessary, that the service person use that cable 15, which bears the same tag-number as the sensor 10.

In the installed state, then the sensor 10, the cable 15 and the holding apparatus 32 have the same tag-number, such as is shown in FIG. 3 on the basis of the tag-number TAGx.

With the aid of the tag-number, it is, thus, assured, that a sensor 10 is installed always only at that measuring location or in that measuring environment assigned to the sensor in step 22 of FIG. 2. An incorrect installation of the sensor 10 is, thus, prevented.

If a sensor 10 provided with a certain tag-number does not agree with the tag-number of the measuring location or the measuring environment, then this can be recognized by the fact that the tag-numbers of the sensor 10, the holding apparatus 32 and the cable 15 do not agree. In this case, for example, such can lead to an error display on the sensor 10 itself and/or on a personal computer connected via the cable 15 and/or to a blocking of the sensor 10 or the entire measuring point.

The description has, to this point, been with reference to a single sensor 10. However, for example, in a plant for sulfuric acid production, a multiplicity of sensors 10 is present. Likewise, it is frequently necessary, that, in the case of a defect in a sensor 10, replacement with a functional sensor 10 must occur, as much as possible, without delay.

The customer has stored, therefore, most often, a number of new sensors 10, as well as also a number of used sensors 10.

In the case of a defect, the service person can return to the measuring location of the defective sensor 10 and, there, read the tag-number of the defective sensor 10 or the associated holding apparatus 32. Then, the service person can retrieve, from the stored new and/or used sensors, that sensor 10', which bears the same tag-number. This selection procedure can be done manually by means of the printed tag-numbers or with the help of a portable computer, which reads the tag-number out of the RFID-chip of the defective sensor 10 and then selects the corresponding sensor 10' from the stored sensors automatically. Then, the service person can replace the defective sensor 10 with the functional sensor 10'.

The same is true also for the procedure of FIG. 2. Also there, after the removal of the sensor 10 according to step 25, immediately, another sensor 10' can be installed in the plant and operated according to step 24. The other sensor 10' can be, in such case, a new or a used, stored sensor 10'. The deinstalled sensor 10 can then be stored, following its new calibrating and/or adjusting according to step 25, in order then later to be installed again in the plant, as a function of its tag-number.

FIG. 4 illustrates a method, with which correct installation of the sensor 10 is automatically checked. In the case of this method, it is assumed that, in step 22 of FIG. 2, the tag-number of the sensor 10 of interest was stored not only in the database of the customer, but also in the sensor 10 itself.

To this end, as was explained above, appropriate memory elements can be provided in the sensor 10.

In a step 41, sensor 10 is installed in the plant by introducing it into the holding apparatus 32 and connecting it to the cable 15. It is assumed that the holding apparatus 32 and the cable 15 have each been assigned a tag-number. Furthermore, it is assumed that the sensor 10 is connected via the cable 15 with a more extensive, measured value processing system, for example, the already mentioned personal computer.

In a step 42, for example, the measured-value processing system checks, whether a tag-number is stored in the sensor 10.

If this is the case, then, in a step 43, for example, the measured-value processing system checks, whether the stored tag-number agrees with an expected tag-number. "Expected tag-number" means that tag-number, which, on the basis of the holding apparatus 32 being used and/or the cable 15 being used, also should be the tag-number of the sensor 10. In the end, thus, in step 43, a comparison is made between the stored tag-number of the sensor 10 and the tag-number of the holding apparatus 32 and/or the tag-number of the cable 15. If a disagreement results in this step with the tag-numbers of the holding apparatus 32 and the cable 15, then an error routine (not shown) is called up. Especially, an error display or a blocking of the sensor 10 or the entire measuring point can be performed.

If the stored tag-number agrees with the expected tag-number, then this means that the right sensor 10 has been connected to the right cable 15. Operation of the sensor 10 is then continued.

If, in step 42, it is ascertained, that no tag-number is stored in the sensor 10, then the service person can, in a step 44, receive a report, that no tag-number is present, and that, therefore, first the step 22 of FIG. 2 must be performed, before the sensor 10 can be used in the plant. Alternatively or in addition, it can be provided in step 44, that the service person is asked, whether, in the context of the method of FIG. 3, a tag-number should be stored in the sensor 10. To the extent that this is answered in the affirmative, the method can be continued with step 43. In this case, it must, however, be heeded, that the tag-number is stored only in the sensor 10, not, however, in the database of the customer.

If, in step 43, it is ascertained, that the stored tag-number does not agree with the expected tag-number, then the service person can be told this in a step 45 and the method of FIG. 3 can then be terminated therewith. In this case, it is necessary, that the service person place another sensor 10 into service. Alternatively or in addition, in step 45, it can be provided, that the service person is asked, whether the tag-number stored in sensor 10 should be over-written. If this is answered in the affirmative, then the method of FIG. 3 can be continued. In this case, the tag-number stored in the sensor 10 no longer agrees, however, with the database of the customer.

The invention claimed is:

1. A method for calibrating and/or adjusting a pH sensor, the pH sensor including evaluating electronics, the method comprising the steps of:
   connecting the pH sensor via an interface to a measured-value processing system or to a USB-port of a personal computer;
   producing a signal by the pH sensor issued to the interface, said signal being essentially not altered by a subsequent transmission from the interface to the measured-value processing system or to the USB-port of the personal computer; and
   calibrating and/or adjusting the pH sensor at a site other than a later measuring location or a later measuring environment, wherein:
   calibration and/or adjusting of the pH sensor occurs in a laboratory.

2. A sensor arrangement, comprising:
   a sensor including evaluating electronics;
   a cable; and
   an interface present between the sensor and the cable, said cable connecting the sensor to a measured-value processing system or to a USB-port of a personal computer, wherein:
   said evaluating electronics includes an amplifier; and
   said evaluating electronics is embodied in such a manner, that a signal produced by the sensor and issued to said interface is essentially not altered by a subsequent transmission via the cable.

3. The sensor as claimed in claim 2, wherein:
   said evaluating electronics includes an analog/digital converter.

4. The sensor as claimed in claim 2, wherein:
   said evaluating electronics includes a memory element.

5. The sensor as claimed in claim 2, wherein:
   the sensor is a pH sensor.

6. The sensor as claimed in claim 5, wherein:
   the cable is connected to the sensor via a coupling, said coupling and the cable have an influence on the signals transmitted from the pH sensor to the measured-value processing system or to the USB-port of the personal computer only to such an extent, that a corruption of the transmitted signals does not take place.

7. A method for calibrating and/or adjusting a sensor, the sensor includes evaluating electronics, the method comprising the steps of:
   producing a signal by the sensor which is essentially not changed by a subsequent transmission to a measured-value processing system or to a USB-port of a personal computer;
   calibrating and/or adjusting the sensor at a site other than a later measuring location or a later measuring environment; and
   assigning the sensor a tag-number, which designates the later measuring location or the later measuring environment, wherein:
   the tag number is applied visibly to the sensor or the tag number is stored in the sensor and in a database or the sensor is provided with an RFID-chip, in which the tag number is stored.

8. The method as claimed in claim 7, wherein:
   the tag-number of the sensor is taken into consideration when installing the sensor into a holding apparatus and/or when connecting the sensor with a cable.

9. The method as claimed in claim 8, wherein:
   a tag-number is likewise assigned to the holding apparatus and/or to the cable.

10. The method as claimed in claim 7, wherein:
    the sensor is a pH sensor.

11. The method as claimed in claim 10, wherein:
    the pH-sensor is connected to a measured-value processing system or the USB-port of the personal computer via a cable.

12. A sensor arrangement including:
    a sensor comprising evaluating electronics; and
    a database; and
    said evaluating electronics, are embodied in such a manner that a signal produced by the sensor is essentially not changed by a subsequent transmission to a measured-value processing system or to a USB-port of a personal computer, wherein:
    the sensor is assigned a tag-number, which designates a later measuring location or a later measuring environment; and
    the tag number is printed or engraved on the sensor, or the tag number is electrically stored in the sensor and in said database, or the sensor is provided with an RFID-chip, in which the tag number is stored.

13. The sensor as claimed in claim 12, wherein:
    the sensor is a pH sensor.

14. The method as claimed in claim 13, wherein:
    the pH sensor is connected to the measured-value processing system or the USB-port of the personal computer via a cable.

15. A method for calibrating and/or adjusting a pH sensor, the pH sensor including evaluating electronics, the method comprising the steps of:
    connecting the pH sensor via an interface to a measured-value processing system or to a USB-port of a personal computer;
    producing a signal by the pH sensor issued to the interface, said signal being essentially not altered by a subsequent transmission from the interface to the measured-value processing system or to the USB-port of the personal computer; and
    calibrating and/or adjusting the pH sensor at a site other than a later measuring location or a later measuring environment, wherein:

the pH sensor is connected to the measured-value processing system or to the USB-port of the personal computer via a cable, said cable being connected to the pH sensor via a coupling; and the signal issued to the interface is essentially not altered by a subsequent transmission via the cable.

16. The sensor as claimed in claim 15, wherein:

the coupling and the cable have an influence on the signals transmitted from the pH sensor to the measured-value processing system or to the USB-port of the personal computer only to such an extent, that a corruption of the transmitted signals does not take place.

* * * * *